Figure 1:
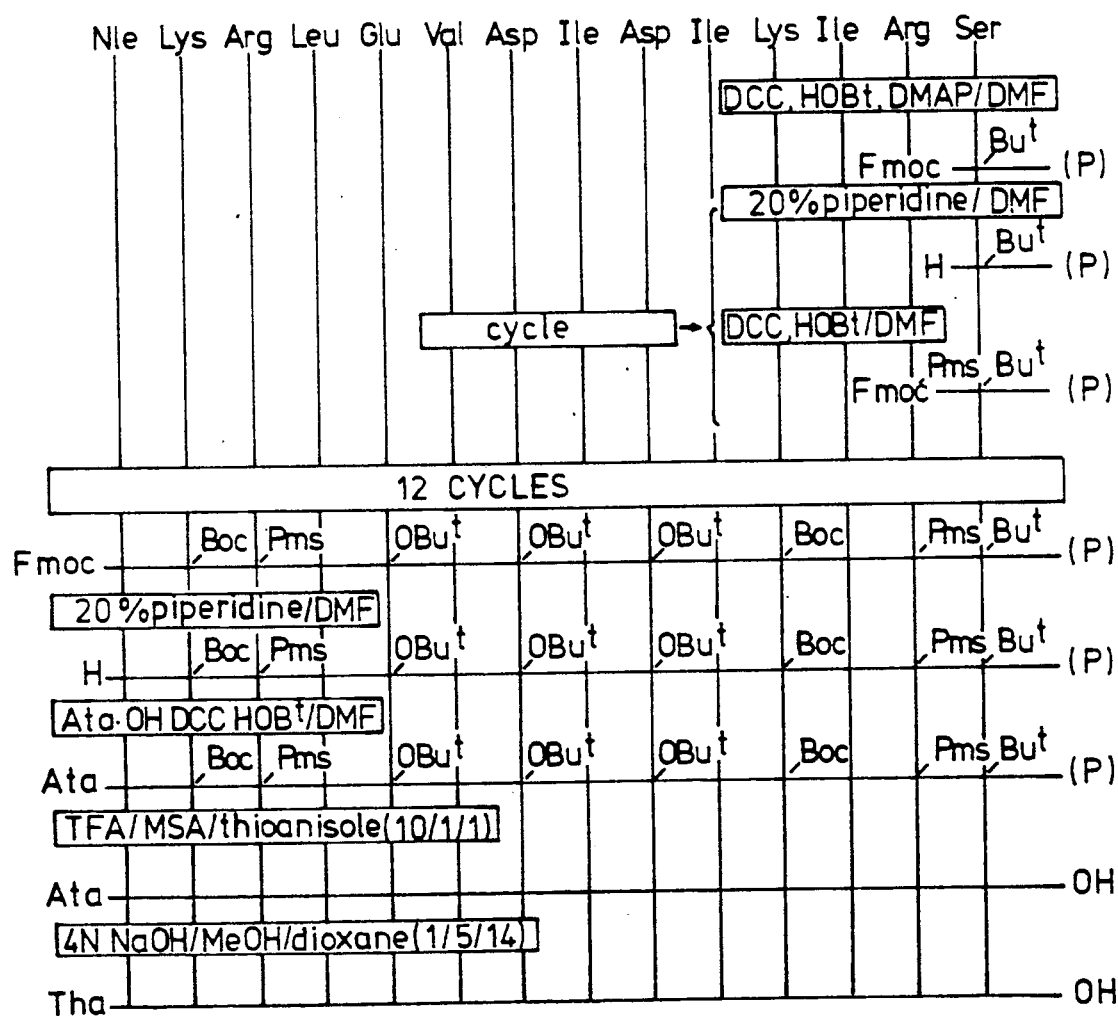

United States Patent [19]

Nieuwenhuizen

[11] Patent Number: 5,099,004

[45] Date of Patent: Mar. 24, 1992

[54] ANTIBODIES AGAINST FIBRIN: IMMUNOGEN TO BE USED FOR THE PREPARATION OF THE ANTIBODIES, PROCEDURE FOR DETERMINING FIBRIN WITH THE ANTIBODIES AND PHARMACEUTICAL PREPARATION BASED ON THE ANTIBODIES

[75] Inventor: Willem Nieuwenhuizen, Bunnik, Netherlands

[73] Assignee: Nederlandse Organisatie Voor Toegepast-Natuurwetenschappelijk Onderzoek TNO, The Hague, Netherlands

[21] Appl. No.: 347,021

[22] Filed: May 4, 1989

[30] Foreign Application Priority Data

May 10, 1988 [NL] Netherlands .................. 8801227

[51] Int. Cl.$^5$ .................. C07K 13/00; C12Q 1/56
[52] U.S. Cl. .................. 530/387.9; 530/382; 530/330; 530/388.25; 530/389.3; 436/518; 436/548; 435/13
[58] Field of Search .............. 530/387, 382, 326–331, 530/806, 807, 808, 809; 435/7, 70.21, 172.2, 240.27, 7.1, 13; 436/518, 548

[56] References Cited

U.S. PATENT DOCUMENTS

| 4,722,903 | 2/1988 | Kudryk et al. | 435/7 |
| 4,851,334 | 7/1989 | Kudryk et al. | 435/7 |
| 4,927,916 | 5/1990 | Matsueda et al. | 530/387 |

FOREIGN PATENT DOCUMENTS

| 0151239 | 8/1985 | European Pat. Off. |
| 87/06263 | 10/1987 | World Int. Prop. O. |
| 88/01514 | 3/1988 | World Int. Prop. O. |

OTHER PUBLICATIONS

Hui et al., Science, vol. 222, pp. 1129–1132, 1983.
Nieuwenhuizen et al., Fibrinogen-Fibrin Formation and Fibrinolysis, vol. 4, pp. 145–192, 1986.
Nieuwenhuizen et al., Biochim. Biophys. Acta, vol. 748, pp. 86–92, 1983.
Nieuwenhuizen et al., Biochim. Biophys. Acta, vol. 755, pp. 531–533, 1983.
Voskuilen et al., Journal of Biological Chemistry, vol. 262, pp. 5944–5946, 1987.
Matsueda et al., Biochemistry, vol. 25, pp. 1451–1455, 1986.
Hui et al., Hybridoma, vol. 5, pp. 215–222, 1986.
Scheefers-Borchel et al., Proc. Natl. Acad. Sci. USA, vol. 82, pp. 7091–7095, 1985.
Liau et al., Thrombosis and Hematosis, vol. 57, pp. 49–54, 1987.
Biological Abstracts, vol. 76, No. 10, Abstract No. 69866, 1983.
Chemical Abstracts, vol. 107, No. 5, Aug. 3, 1987, p. 359, Abstract No. 36045K.
Kudryk et al., Molecular Immunology, vol. 21, No. 1, pp. 89–94, 1984.
Chemical Abstracts, vol. 103, No. 17, Oct. 28, 1985, Abstract No. 139994R.
Roitt, I., Essential Immunology, Sixth Edition (Blackwell Scientific Publications, Boston), pp. 55–56 (1988).
W. Schielen et al., "The sequence Aα-(148-160) in fibrin, but not in fibrinogen, is accessible to monoclonal antibodies", Proc. Natl. Acad. Sci. USA, vol. 86, pp. 8951–8954, Nov. 1989.

*Primary Examiner*—Esther L. Kepplinger
*Assistant Examiner*—Carol A. Spiegel
*Attorney, Agent, or Firm*—Bachman & LaPointe

[57] ABSTRACT

Antibodies are provided, which are directed against a sequence of amino acids corresponding to amino acids from the sequence 111–207, in particular 148–161, of the Aα-chain of fibrinogen. These novel antibodies react specifically with fibrin, both type I and type II, and not with fibrinogen. They are effective in detecting, preventing and treating blood clot formation.

5 Claims, 1 Drawing Sheet

ANTIBODIES AGAINST FIBRIN: IMMUNOGEN TO BE USED FOR THE PREPARATION OF THE ANTIBODIES, PROCEDURE FOR DETERMINING FIBRIN WITH THE ANTIBODIES AND PHARMACEUTICAL PREPARATION BASED ON THE ANTIBODIES

The invention relates to antibodies which react specifically with fibrin.

The fibrinopeptides A of the A$\alpha$ chains and the fibrinopeptides B of the B$\beta$ chains are consecutively cleaved off enzymatically by thrombin from the fibrinogen normally present in blood, to form respectively monomeric fibrin type I and monomeric fibrin type II. Said monomeric fibrins are able to remain in solution up to a certain concentration. At higher concentration, monomeric fibrin may polymerize to form a fibrin clot. To identify an impending formation of a fibrin clot (thrombosis) in good time and to be able to prevent blood clots (thrombi) in the blood vessels, an early detection of fibrin in the blood is therefore desirable, and at the same time the means of detection must distinguish between the fibrinogen and the fibrin itself.

This detection may in principle be carried out with the aid of antibodies against fibrin. Most of the antibodies against fibrin investigated, however, cannot be used because they also react with fibrinogen. Kudryk et al. (Molecular Immunology 21, 89-94 (1984)) have described a monoclonal antibody which is induced by fibrin fragments as antigens and binds to the amino end of the $\beta$-chain of fibrin. Hui et al. (Hybridoma 5, 215-222 (1986)) have also described an antibody which is obtained by immunizing with a peptide from the $\beta$-chain end of fibrin.

Said antibodies have, however, the disadvantage that they identify only the amino end of the fibrin $\beta$-chain which is liberated after the fibrinopeptide B is cleaved off and they can therefore not be used for detecting fibrin I.

European patent application 152,612 describes a procedure for determining fibrin with the aid of an antibody which is induced by immunizing an animal with a peptide from the new amino end of the $\alpha$-chain, which is produced by cleavage of fibrinopeptide A. In particular, this involves the amino end of the $\alpha$-chain of fibrin.

Antibodies have now been found which act very specifically against fibrin and which can be obtained by immunizing an animal with an immunogen which comprises a section of the amino acid sequence of fibrin, which section is not active in immune reactions in fibrinogen but is active in immune reactions in fibrin type I and type II.

The antibodies according to the invention are characterized in that they are directed against a peptide having a sequence of 3-97 amino acid residues, at least three of which are located in the same relative position as the same amino acid residues in the amino acid sequence 111-207 of the A$\alpha$-chain of fibrinogen.

The antibodies according to the invention do not only react with fibrin type I and fibrin type II, but also with some degradation products of fibrin. Thus, they react with fragments D-dimer, D-EGTA, and with the A-chain, whereas they do not react with fragments D-cate, E, X, Y and B-chain. International Patent Application WO 88.01514 describes a monoclonal antibody against fibrin, which is raised using human fibrin as an antigen and not with a specific sequence of fibrin as according to the present invention. The antibody of WO 88.01514 cross-reacts maximally with fragment D-dimer and minimally with fragments D, X, Y and A-chain, thus showing a different immunospeicificity from the present antibodies.

Preferably, 5 or more amino acid residues of the peptide are located in the same relative position as the same amino acid residues in the amino acid sequence 148-197 of the A$\alpha$-chain of fibrinogen and, in particular, as the same amino acid residues in the amino acid sequence 148-161. To prepare antibodies according to the invention, the 148-160 sequence (Lys-Arg-Leu-Glu-Val-Asp-Ile-Asp-Ile-Lys-Ile-Arg-Ser), a tridecapeptide, is found to be very suitable.

The immunogenic amino acid sequence can be prepared in a known manner, for example by a standard SPPS method such as that described by Stewart J. M. and Young J. D. in "Solid Phase Peptide Synthesis", Pierce Chemical Co., 2nd impression, 1984. In this case, the side chains of amino acids which contain a functional group and which may not participate in the coupling reaction are reversibly protected. The free carboxyl group of a derivatized amino acid is activated and thus caused to react with the amino group of the derivatized amino acid to be coupled. This activation can be carried out with DCC (the abbreviations are explained below), DCC/HOBt or DCC/HONSu. Activation with DCC/HOBt is preferred.

Boc, Fmoc or Trt can be used as protective group for the $\alpha$-amino function of the amino acids. Protection with Fmoc is preferred.

The side chain functions such as carboxyl, hydroxyl, guanidino and amino groups, can be protected in accordance with their reactivity with the protective groups usual in peptide chemistry. To protect the carboxyl groups in Asp and Glu, use may be made of aliphatic or aromatic residues derived from alcohols such as methanol, tert-butanol or benzyl alcohol. In the connection, tert-butanol is preferred. The hydroxyl group of Ser may also be protected by means of etherification with tert-butanol. To protect the guanidino function of Arg, use may be made of the tosyl, nitro or Pms group or of protonation. The Pms group is preferred. The $\epsilon$-amino group of Lys may be protected by means of the Boc or Msc group. In this case, the Boc group is preferred. In view of the low stability in relation to bases of the protective group for the $\alpha$-amino function (Fmoc), the bond of the first amino acid to the solid resin must be stable towards bases. Anchoring to the so-called p-alkoxybenzyl alcohol resin produces an ester bond labile in acid medium and said anchoring is preferred in this case.

The optional "spacer", the section which joins the end of a synthetic peptide to a carrier protein, may have various structures. The compounds suitable for this purpose contain, for example, two identical or two different reactive groups at the ends of an alkyl group containing, for example, 2 to 8 atoms. This group includes, inter alia, dialdehydes such as glutaraldehyde, dissocyanates such as 1,6-hexamethylene diisocyanate, diamines such as 1,6-hexamethylenediamine or $\omega$-aminocarboxylic acids such as $\epsilon$-aminocaproic acid or $\epsilon$-maleimidocaproic acid. These bifunctional reagents are combined, after activation if necessary, in a known manner with the synthetic peptide on the one hand and with the carrier protein on the other hand, $\epsilon$-Maleimidocaproic acid is preferred as a section of the total "spacer". The other section of the "spacer" may consist of a mercaptoacetyl group derived from acetylthioacetic acid and the synthetic amino acid norleucine (Nle).

to introduce the "spacer", the protected peptide is acylated with Nle and acetylthioacetic acid when it is still bound to the resin.

The ε-maleimidocaproic acid is activated by means of HONSu and DCC to form maleimidohexanoyl-N-hydroxysuccinimide. After adding a carrier protein, aminolysis of the active ester molecules by the free amino groups of the carrier protein takes place.

After cleaving off the resin, and deprotecting and purifying the peptide which is extended by a section of the "spacer", the amino terminal part is deprotected, for example by treatment with a mixture of 4N NaOH/methanol/dioxane (1/15/14), which cleaves off the acetyl group. The coupling between the carrier protein provided with a maleimido group and the synthesized peptide extended with a mercaptocacetyl group proceeds spontaneously.

In principle, any protein can be used as carrier protein, for example bovine serum albumin (BSA).

The immunogen thus obtained can be used to immunize laboratory animals such as mice, rates, rabbits or goats in the known manner. In this manner, antisera containing polyclonal antibodies are obtained.

Preferably, monoclonal antibodies are induced in a corresponding manner, for instance in accordance with Kohler, G. and Milstein, C., Nature 256 (1975), 495-497. The known mouse myeloma cell lines can be used for this purpose. Favourable results are obtained by using a cell line which does not itself produce immunoglobulin.

Spleen cells of immunized Balb/c mice are fused with a myeloma cell line (preferably, the cell lines Sp 2/0 Ag14 or P3×63 Ag 8653) which does not produce immunoglobulin. The fused cells are selected by culturing in a selection medium in which unfused spleen cells and myeloma cells die and in which only spleen cells which are fused with the myeloma cells (hybridoma cells) survive. After this selection step, the hybridoma cells which produce fibrin-specific antibodies are selected in an ELISA system. The hybridoma cells which produce fibrin-specific antibodies are introduced into the abdominal cavity of Balb/c mice where they grow and produce ascitic fluid which can be tapped off and which is used as a source for purifying the required monoclonal antibodies.

The invention also relates to an immunogen which can be used to prepare antibodies against fibrin such as described above.

The antibodies according to the invention do not react with fibrinogen but do react with fibrin type I and type II. The sensitivity of this reaction is of the order of 0.1 μg/ml, which sensitivity is not restricted by the fibrinogen which is present in a 20,000-fold excess.

The advantage of determining fibrin type I is that the very first step in the clotting is the formation of fibrin I. Because the determination of "soluble fibrin" is aimed precisely at detecting the very earliest clotting, a test directed at fibrin I has a higher diagnostic value than one which is directed only at fibrin II. The formation of fibrin II proceeds via fibrin I.

A further advantage of the antibodies according to the invention is that they are directed against a site in the fibrin which is involved in accelerating the activation of plasminogen by t-PA (tissue plasminogen activator), i.e. in accelerated plasmin formation. Complexing of this site with the antibody with counteract the acceleration and thus assist in keeping the fibrin present in plasma intact during the determination thereof. This is not possible with the antibodies against fibrin known hitherto.

The invention therefore also relates to a procedure for detecting and determining fibrin, in particular in blood, with the aid of an antibody such as described above.

This can be carried out, for example with a so-called "sandwich" ELISA or "sandwich" EIA.

In this process, the purified monoclonal antibody is immobilized on a solid carrier and brought into contact in that form with the fluid (blood/plasma) in which it is desired to determine the fibrin content. Then the quantity of fibrin thus bound by the monoclonal antibodies is determined by adding a second antibody which is labelled with a detectable label such as a radioactive atom, a fluorescent or luminescent group or, in particular, an enzyme (for example, horseradish peroxidase (HRP)). The quantity of the bound second antibody is then determined by measuring the activity, for example the enzyme activity, of the label. Said activity is a measure of the fibrin concentration in the blood or plasma used.

A possible embodiment of the procedure is to detect fibrin by using a second labelled antibody which identifies another epitope of fibrin. In that case, the monoclonal antibody described here can be used in immobilized form and the second as HRP conjugate. Although, according to the invention, the first antibody is more than adequately fibrin-specific, the specificity of the detection method is, if possible, still further improved by using a second antibody which also identifies fibrin.

The invention also relates to a kit for determining fibrin which contains an antibody such as described above, for example in an antiserum, and also further constituents required to determine fibrin.

Because the antibodies according to the invention are fibrin-specific, they can also be used to detect and to localize fibrin in vivo (in particular, blood clots). For this purpose, the antibodies are labelled with a substance which can be detected outside the body, This is, for example, $Tc^{99m}$, which can be detected because it is radioactive and emits (γ) radiation. The method described by Feitsma in Nucl. Med. Comm. 8 (1987), 771-777 is particularly suitable for this purpose. The fibrin specificity may also be used to direct an active substance, in particular a substance which is effective in dissolving blood clots, to the site of the clots, This results in a higher effectiveness for the active substance. A combination of a tissue-type plasminogen activator or other plasminogen activators, plasminogen, plasmin or other proteases, with antifibrin antibodies is conceivable. Examples of this principle are described by M. S. Runge et al., Proc. Natl. Acad. Sci. 84 (1987), 7659-7662 and C. Bode et al., J. Biol. Chem. 262 (19870, 10819-10823.

The invention also relates to a pharmaceutical preparation which contains an active substance of this type coupled to an antibody as described above. Said active substance is preferably a fibrinolytic agent. Examples of fibrinolytic agents are tissue-type plasminogen activator (or variants thereof obtained by means of recombinant DNA techniques) and also urine-type plasminogen activator (U-PA), streptokinase, plasmin, plasminogen.

In the above and in the examples below, the abbreviations used have the following meanings:

Ata-Ohacetylthioacetic acid
BSA bovine serum albumin
Boc tert-butoxycarbonyl
But tert-butyl
CCD counter current distribution
DCC dicyclohexylcarbodiimide
DMAP 4-dimethylaminopyridine
DMF dimethylformamide
Fmoc 9-fluorenylmethoxycarbonyl
HOBt 1-hydroxy-1H-benzotriazole
HONSu N-hydroxysuccinimide
MHS 6-(maleimido)hexanoyl-N-hydroxysuccinimide
MSA methanesulfonic acid
Msc methylsulfonylethoxycarbonyl
Nle D,L-norleucine
(P) p-alkoxybenzyl alcohol resin
PBS phosphate-buffered saline solution (pH=6.9, 0.15 M NaCl)
Pms pentacmthylphenylsulfonyl
SPPS solid phase peptide synthesis
Tha mercaptoacetyl
TFA trifluoroacetic acid
TLC thin-layer chromatography
Trt trityl

EXAMPLE I

The fibrinogen Aα-(148-160)-tridecapeptide: H-Lys-Arg-Leu-Glu-Val-Asp-Ile-Asp-Ile-Lys-Ile-Arg-Ser-OH was prepared on a p-alkoxybenzyl alcohol resin (Bachem, Bubendorf, Switzerland) with the aid of a semiautomatic peptide producer (Labortec SP-640, Bubendorf, Switzerland). The amino acids were coupled in the given sequence as Fmoc-amino acids by a standard procedure, starting with the C-terminal serine. In this process, the following protective groups were used for the side chains: Lys: Boc; Arg: Pms; Glu, Asp and Ser: Bu$^t$. The amino acids were coupled by means of DCC/HOBt. The resin was finally deblocked and released by treating with TFA/MSA/thioanisole (10/1/1) for 2 hours at room temperature, followed by filtration, precipitation with ether and lyophilizaiton from water. The crude peptide was purified with the aid of CCD in an apparatus with elements of 10 ml of subphase supplied by Labortec, Bubendorf, Switzerland, Use was made of the butnaol/acetic acid/water system (5/1/4). Samples from the maxima were hydrolysed in 5.7 N hydrochloric acid at 105° C. for 48 hours in sealed glass ampules evacuated at −80° C. The hydrolysate was evaporated several times with water and subjected to amino acid analysis in a JEOL-JLC-6AM analyzer.

EXAMPLE II

The tridecapeptide derivative provided with a section of the "spacer", mercaptoacetyl-DL-norleucylfibrinogen-Aα(148-160)-tridecapeptide (hereinafter termed "tridecapeptide") was obtained by the systhesis scheme shown in FIG. 1.

After 200 steps, two compounds having the Nernst distribution coefficients: (cpd. 1) D=0.38 (r=55) and (cpd. 2) K=0.74 (r=85) were isolated from the mixture of diastereomers. The two compounds were obtained in equal quantities. Samples from the maxima were hydrolsyed in 5.7 N hydrochloric acid at 105° C. for 48 hours in sealed glass ampules evacuated at −80° C. The hydrolysate was evaporated several times with water and subjected to amino acid analysis in JEOL-JLC-6AM analyzer.

After purification by means of CCD, the peptide was characterized by means of TLC and amino acid analysis; the norleucine was included in order to be able to carry out the amino acid analysis of the conjugates to be prepared. The chemical purity was determined by means of TLC in several eluting systems.

EXAMPLE III 4.5 mg of MHS were added to 50 mg of very pure BSA dissolved in 1 ml of phosphate buffer (pH=8). After reacting for 5 minutes, the reaction mixture was purified by means of gel filtration through A SEPHADEX G-25 filter with phosphate buffer (pH=6) as eluent.

37 mg of the activated peptide from Example II were added to the BSA-spacer solution thus obtained. After reacting for 2 hours at room temperature, the reaction mixture was dialyzed against PBS and lyophilyzed.

EXAMPLE IV

Polyclonal antibodies

A monotonically N-terminally coupled peptide-carrier protein conjugate is dissolved in 0.15 M NaCl and mixed with an equal volume of Freund's complete adjuvant. A volume of this mixture equivalent to 125 μg of total protein (10 μg of coupled peptide) is injected into the abdominal cavity of Balb/c mice. These injections are repeated 4 times, but Freunds incomplete adjuvant is now used.

The presence of antibodies in the blood of the mice thus immunized is detected via the ELISA described for this purpose.

EXAMPLE V

Monoclonal antibodies

The Balb/c mice immunized according to Example IV are intravenously injected with 250 g of BSA-peptide conjugate dissolved in 0.15 M NaCl 3 days before the removal of their spleen. Spleen cells from the mice are mixed with myeloma cells in a ratio of 4:1 in the presence of 40% polyethylene glycol (molecular weight 4000) as described by K,öhler and Milstein (Nature 256 (1975), 495–497). After fusion, the cell suspension is diluted and distributed over the wells of 4 microtiter plates so that each well contains $3.3 \times 10^5$ spleen cells.

After the spleen cells and the myeloma cells have dies in the selection medium according to Köhler and Milstein, the culture fluids of the wells which show hybridoma growth are tested after 10–14 days for the presence of fibrin-specific antibodies.

For this purpose, the wells of polystyrene microtiter plates are coated with fibrinogen or fibrin monomers (prepared according to Belitzer et. al., Biochim, Biophys. Acta 154 (1968), 367). After washing, small volumes of the culture fluids of the hybridomas are placed in the coated wells and incubated therein for 1 hour at 37° C. The wells are then washed again. A solution of polyclonal antibodies directed against mouse immunoglobins and coupled with horseradish peroxidase is the introduced into the wells and incubated therein for 1 hour at 37° C. After washing, the presence of peroxidase activity in the wells is determined and quantified as a measure of the quantity and specificity of the monoclonal antibodies present in the culture fluid.

The cell lines which produce a fibrin-specific antibody are then cloned two more times as described by McKearn (T. J. McKearn in "Monoclonal Antibodies, Hybridomas; a new dimension in biological analysis, Plenum, N.Y., 1980, page 374).

Examples of two cell lines which were found in this way are:

| Antigen used | result of ELISA | |
|---|---|---|
| | cell line I | cell line II |
| Fibrinogen | 0.009 | 0.000 |
| Fibrin monomer | 0.653 | 0.447 |

EXAMPLE VI

Determination of fibrin in blood

Fresh plasma from healthy donors is treated for a short time with a small quantity of thrombin. This produces a quantity of soluble fibrin in said plasma. A solution (10 μg/ml) of a monoclonal antibody prepared according to the invention (in 0.04 M Tris/HCl, pH 7.5) is placed in the wells of a polystyrene microtiter plate and incubated therein for 16 hours at 4° C. During this incubation, the monoclonal antibodies are adsorbed on the wall of the wells. After washing, dilution series of the plasma treated with thrombin and of the same plasma without thrombin treatment are pipetted into the wells. After incubating for 1 hour, preferably at 4° C., the wells are washed and a solution of a horseradish peroxidase conjugate with another monoclonal antibody (which does not need to be fibrin-specific) is placed in the wells. After incubating again for 1 hour (preferably at 4° C.), the wells are washed and the peroxidase activity is used as a measure of the quantity of fibrin which is bound by the wells coated with fibrin-specific antibody. This is done by using a mixture of tetramethylbenzidine and hydrogen peroxide as a substrate for peroxidase (E. S. Bos et al., J. Immunoassay 2 (1981), page 187). The action of peroxidase produces in this way a blue product which turns yellow when the reaction is terminated by adding 1 M $H_2SO_4$ after 10 minutes incubation at 37° C. The intensity of the yellow colour is measured at a wavelength of 405 nm and is a measure of the peroxidase activity.

An example:

| | Optical density found at 405 nm for the plasma dilutions: | | | | |
|---|---|---|---|---|---|
| | 1/20 | 1/60 | 1/180 | 1/540 | 1/1620 |
| Untreated plasma | 0.046 | 0.019 | 0.007 | 0.003 | 0.001 |
| Plasma treated with thrombin | 1.294 | 1.272 | 0.996 | 0.371 | 0.054 |

I claim:

1. Isolated antibodies which specifically bind fibrin types I and II but do not specifically bind fibrinogen, the antibodies being directed against a peptide having a sequence of 5-97 amino acid residues, at least five of which correspond to the sequence of amino acid residues in the amino acid sequence 111-207 of the Aα-chain of fibrinogen.

2. Antibodies according to claim 1, wherein they are directed against a peptide with a sequence of 5-50 amino acid residues, at least five of which correspond to the sequence of amino acid residues in the sequence Aα-148-197.

3. Antibodies according to claim 2, wherein they are directed against a peptide having a sequence of 5-14 amino acid residues, at leave five of which correspond to the sequence of amino acid residues in the sequence Aα148-161.

4. Antibodies according to claim 3 wherein they are directed against a peptide comprising the amino acid sequence Aα148-160.

5. A monoclonal antibody which specifically binds with fibrin types I and II but does not specifically bind fibrinogen, the monoclonal antibody being directed against a peptide having a sequence of 5-97 amino acid residues, at least five of which correspond to the sequence of amino acid residues in the amino acid sequence 111-207 of the Aα-chain of fibrinogen.

* * * * *